United States Patent [19]

Alig et al.

[11] 4,252,729

[45] Feb. 24, 1981

[54] STEROIDS AND PROCESS FOR THEIR MANUFACTURE

[75] Inventors: Leo Alig, Kaiseraugst; Andor Fürst, Basel; Marcel Müller, Frenkendorf, all of Switzerland; Ulrich Kerb; Rudolf Wiechert, both of Berlin, Fed. Rep. of Germany

[73] Assignee: Hoffmann-La Roche Inc., Nutley, N.J.

[21] Appl. No.: 36,477

[22] Filed: May 7, 1979

[30] Foreign Application Priority Data

May 12, 1978 [CH] Switzerland .................. 5208/78

[51] Int. Cl.$^3$ .................. A61K 31/56; C07J 9/00
[52] U.S. Cl. .................. 260/397.1; 424/243; 204/157.1 R
[58] Field of Search .................. 260/397.1

[56] References Cited

U.S. PATENT DOCUMENTS

| 3,856,828 | 12/1974 | Phillipps et al. | 260/397.1 |
| 4,061,661 | 12/1977 | Kerb et al. | 260/397.45 |

OTHER PUBLICATIONS

Breslow et al., "J.A.C.S." vol. 99, No. 3 (1977), pp. 905-915.

*Primary Examiner*—Elbert L. Roberts
*Attorney, Agent, or Firm*—Jon S. Saxe; George M. Gould; John B. Wilson

[57] ABSTRACT

The present disclosure is concerned with 9α-chloro-17-(m-iodobenzyloxy) steroids and a process for their manufacture. The subject compounds are useful as intermediates in the synthesis of pharmacologically-active substances and have themselves been found to exhibit pharmacological activity.

6 Claims, No Drawings

STEROIDS AND PROCESS FOR THEIR MANUFACTURE

BACKGROUND OF THE INVENTION

Breslow et al., e.g., *J. Amer. Chem. Soc.* 96 (1974) 1973, ibid. 96 (1974) 6791, describe the chlorination of steroids which have been esterified at the 3α-position wherein the tertiary carbon atom in the 9-position is chlorinated with iodobenzene dichloride under the influence of light, and subsequently, hydrogen chloride is cleaved off with the formation of a 9,11-double bond.

The disadvantage in the foregoing process is that it has utility in only those steroids which have no carboxy group or no unprotected carbonyl group in the 17β-side chain. In accordance with the present invention, it has been found that 9α-chloro-3-oxo-androst-4-ene-17β-carboxylic acids can be selectively obtained in the unprotected form. It has further been found that the chlorination is effected selectively in the 9-position which is unexpected since, from the work of Halpern, e.g., Chem. & Ind. (1962), 1571, it was known that steroids with double bonds react with iodobenzene dichloride to give the corresponding α-dichlorosteroids.

SUMMARY OF THE INVENTION

A steroid of the formula:

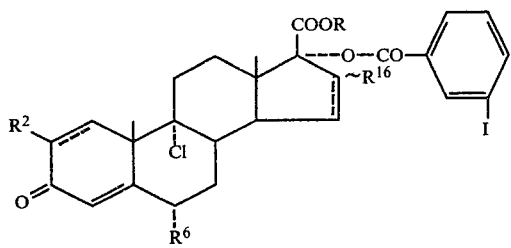

Formula I wherein R represents a hydrogen atom or a lower alkyl group, $R^2$ represents a hydrogen or chlorine atom, $R^6$ represents a hydrogen or fluorine atom or a methyl group, $R^{16}$ represents a hydrogen atom or an α-methyl, β-methyl, methylene or α-hydroxy group and the broken lines in the A and D-rings denote optional bonds with the proviso that the D-ring can be unsaturated only when $R^{16}$ represents a methyl group.

The term "lower alkyl" used herein means, in particular, alkyl groups which are the characterizing groups of alkanols containing up to 4 carbon atoms; for example, methyl, ethyl, propyl, isopropyl, butyl and isobutyl.

A preferred class of steroids of formula I comprises those in which $R^2$, $R^6$ and $R^{16}$ each represent a hydrogen atom.

The steroids of formula I are primarily intermediates for the manufacture of pharmacologically-valuable substances. However, they themselves also have pharmacological (e.g., hormonal) activity.

DETAILED DESCRIPTION OF THE INVENTION

Examples of steroids of formula I are:
9α-chloro-17-(m-iodobenzoyloxy)-3-oxo-androst-4-en-17β-carboxylic acid,
2,9α-dichloro-17-(m-iodobenzoyloxy)-3-oxo-androsta-1,4-diene-17β-carboxylic acid,
9α-chloro-6α-fluoro-17-(m-iodobenzoyloxy)-3-oxo-androst-4-ene-17β-carboxylic acid,
9α-chloro-6α-fluoro-17-(m-iodobenzoyloxy)-3-oxo-androsta-1,4-diene-17β-carboxylic acid,
9α-chloro-17-(m-iodobenzoyloxy)-6α-methyl-3-oxo-androst-4-ene-17β-carboxylic acid,
9α-chloro-17-(m-iodobenzoyloxy)-6α-methyl-3-oxo-androsta-1,4-diene-17β-carboxylic acid,
9α-chloro-17-(m-iodobenzoyloxy)-16α-methyl-3-oxo-androst-4-ene-17β-carboxylic acid,
9α-chloro-17-(m-iodobenzoyloxy)-16α-methyl-3-oxo-androsta-1,4-diene-17β-carboxylic acid.
9α-chloro-17-(m-iodobenzoyloxy)-16β-methyl-3-oxo-androst-4-ene-17β-carboxylic acid,
9α-chloro-17-(m-iodobenzoyloxy)-16β-methyl-3-oxo-androsta-1,4-diene-17β-carboxylic acid,
9α-chloro-17-(m-iodobenzoyloxy)-16-methyl-3-oxo-androsta-4,15-diene-17β-carboxylic acid,
9α-chloro-17-(m-iodobenzoyloxy)-16-methyl-3-oxo-androsta-1,4,15-triene-17β-carboxylic acid,
9-chloro-16α-hydroxy-17-(m-iodobenzoyloxy)-3-oxo-androst-4-en-17β-carboxylic acid,
9α-chloro-16α-hydroxy-17-(m-iodobenzoyloxy)-3-oxo-androsta-1,4-diene-17β-carboxylic acid,
9α-chloro-17-(m-iodobenzoyloxy)-16-methylene-3-oxo-androst-4-ene-17β-carboxylic acid,
9α-chloro-17-(m-iodobenzoyloxy)-16-methylene-3-oxo-androsta-1,4-diene-17β-carboxylic acid, and the methyl, ethyl, propyl and butyl esters of these acids.

After cleaving the 9α-chlorine atom from the steroids of formula I, there are obtained according to methods known per se, such as, for example with silver perchlorate in the warm, with an alkali or alkaline earth metal carbonate in dimethylformamide or an organic base such as collidine, lutidine and pyridine or with an alkali hydroxide in an alcoholic solvent, the corresponding $\Delta^{9(11)}$-steroids. In the latter method, ester groups which may be present are simultaneously also cleaved. The thus-obtained $\Delta^{9(11)}$-steroids are valuable starting materials for the manufacture of known 9α,11β-dihalosteroids or 11β-hydroxy-steroids such as, for example, the steroids known from U.S. Pat. Nos. 3,828,080 and 3,856,828.

The 9α,11β-dihalo-steroids are obtained, as is well known, by adding bromine fluoride, chlorine fluoride or chlorine to a $\Delta^{9\,(11)}$-steroid. The 11β-hydroxy-9α-fluoro-steroids are obtained, as is well known, by adding hypobromous acid to a corresponding $\Delta^{9\,(11)}$-steroid, converting a resulting 11β-hydroxy-9α-bromo-steroid by hydrogen bromide cleavage into a 9β,11β-oxido-steroid and opening the epoxide ring with hydrogen fluoride. In order to obtain an 11β-hydroxy-steroid, an 11β-hydroxy-9α-bromo-steroid can also be debrominated with tributyltin hydride, Raney-nickel or chromium-(II) chloride.

The steroids of formula I have the particular advantage that they offer a ready access to the 11β-hydroxy-steroids which hitherto have been manufactured by microbiological hydroxylation. Whereas in microbiological methods costly provisions must be made (cultivation of the microorganisms, sterility of all fermentation media, large volumes), the 11β-hydroxy-steroids can be manufactured from the steroids of formula I by steps which are technically simple to realize.

The invention is also concerned with a process for the manufacture of the steroids of formula I which process is characterized in that a steroid of the general formula:

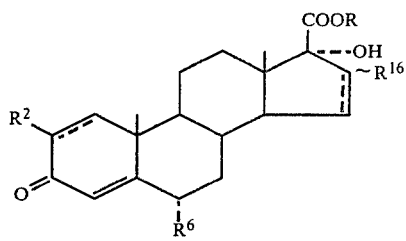

Formula II wherein R, $R^2$, $R^6$, $R^{16}$ and the broken lines in the A and D rings have the significance given earlier, is esterified with an m-iodobenzoylating agent, if desired a free 17β-carboxy group is esterified and the resulting 17α-m-iodobenzoyl ester is treated with chlorine, sulphuryl chloride or iodobenzene dichloride and irradiated with long-wave UV-light or heated in the presence of a radical-former and, if desired, a free 17β-carboxy group is esterified.

The process provided by the present invention is conveniently carried out by reacting a steroid starting material of formula II with an m-iodobenzoylating agent such as m-iodobenzoyl chloride or anhydride in the presence of an acid-binding agent (e.g., pyridine or triethylamine) or in the presence of a strong acid catalyst (e.g., p-toluenesulphonic acid). As the solvent for the m-iodobenzoylation, there come into consideration organic solvents which do not contain hydroxyl groups (e.g., chlorinated hydrocarbons such as methylene chloride or hydrocarbons such as benzene). Thereby there is initially obtained a mixed anhydride of the steroid carboxylic acid and the m-iodobenzoic acid, which is cleaved by means of an acid (e.g., with aqueous acetic acid) or by means of a base (e.g., with aqueous diethylamine) to give the desired 17α-m-iodobenzoyloxy derivative of the steroid starting compound II.

The conversion of a thus-obtained 17α-(m-iodobenzoyl)-steroid ester into a corresponding steroid of formula I is conveniently carried out in a suitable solvent. Suitable solvents are those which are not affected by the halogenating agent which is used, examples of such solvents being halogenated hydrocarbons such as methylene chloride, chloroform, carbon tetrachloride, trichloroethylene or dichloroethylene and aromatic hydrocarbons such as benzene, chlorobenzene or toluene. If desired, these solvents can also be used as mixtures with one another. Conveniently, the conversion is carried out with the exclusion of oxygen in a protective gas atmosphere. For this purpose, an inert gas such as nitrogen or argon is conducted into the solution. The irradiation with long-wave UV-light can be carried out using a commercially-obtainable ultraviolet emitter (e.g., a mercury high-pressure lamp). As the radical-former, there can be used an organic peroxide such as dibenzoyl peroxide, copper-(I) acetate or azodiisobutyronitrile. Conveniently, there are used 1 to 25, preferable 10, equivalents of the radical-former per 100 equivalents of the steroid to be chlorinated in a solvent; for example, one of the aforementioned halogenated hydrocarbons.

The esterification of a free 17β-carboxy group can be carried out according to methods known per se; for example, with a diazoalkane such as diazomethane in ether, or by reaction of a salt of the 17β-carboxylic acid (e.g., an alkali salt) with an alkyl halide such as methyl iodide.

The steroid starting materials of formula II, insofar as they are not known or are described hereinafter, can be prepared in analogy to known methods or methods described in the examples.

The steroids of formula I have hormonal activity, especially on the endocrine system, and can accordingly be used as hormonally-active agents (e.g., as progestational agents). They can be administered orally or parenterally. As dosage guidelines, there come into consideration 0.005 mg/kg to 0.15 mg/kg per day.

The steroids of formula I can be used as medicaments; for example, in the form of pharmaceutical preparations which contain them in association with a compatible carrier material. The carrier material can be an organic or inorganic inert carrier material which is suitable for enteral, percutaneous or parenteral administration such as, for example, water, gelatin, gum arabic, lactose, starch, magnesium stearate, talc, vegetable oils, polyalkyleneglycols, petroleum jelly, etc. The pharmaceutical preparations can be made up in solid form (e.g., as tablets, dragees, suppositories or capsules), in semi-solid form (e.g., as salves) or in liquid form (e.g., as solutions, suspensions or emulsions). The pharmaceutical preparations may be sterilized and/or may contain adjuvants such as preserving, stabilizing, wetting or emulsifying agents, salts for varying the osmotic pressure or buffers. The pharmaceutical preparations can also contain other therapeutically-valuable substances.

The following examples illustrate the process provided by the present invention:

DESCRIPTION OF THE PREFERRED EMBODIMENTS

EXAMPLE I 1 g of 17-hydroxy-3-oxo-androst-4-ene-17β-carboxylic acid is reacted in 30 ml of methylene chloride in the presence of 1.4 ml of triethylamine with 1 ml of m-iodobenzoyl chloride for 2 hours at 0° C. The mixed anhydride intermediate is cleaved by the addition of aqueous sodium carbonate solution. There are obtained 1.48 g of 17-(m-iodobenzoyloxy)-3-oxo-androst-4-ene-17β-carboxylic acid of melting point 235°–236° C.; $\epsilon_{220}=33{,}600$; $[\alpha]_D=-22°$ (dioxan, c=0.1%).

1.68 g of 17-(m-iodobenzoyloxy)-3-oxo-androst-4-ene-17β-carboxylic acid and 825 mg of iodobenzene dichloride were gasified with argon in 340 ml of chloroform and exposed for 20 minutes with a mercury high-pressure lamp. The solution was washed with dilute sodium bisulphite solution and water, dried and evaporated in vacuo. Chromatography on silica gel gave 9α-chloro-17-(m-iodobenzoyloxy)-3-oxo-androst-4-ene-17β-carboxylic acid of melting point 236°–237° C.; $[\alpha]_D=-40°$ (dioxan, c=0.1%); $\epsilon_{220}=34{,}900$.

1.02 g of 9α-chloro-17-(m-iodobenzoyloxy)-3-oxo-androst-4-ene-17β-carboxylic acid were treated in 100 ml of acetone with 1 g of silver perchlorate in 30 ml of water, and the mixture was boiled at reflux for 4 hours under argon. After the addition of 2 ml of saturated sodium chloride solution, the mixture was filtered and concentrated in vacuo. The residue was diluted with methylene chloride and washed with dilute sodium chloride solution. The dried solution was evaporated, and the 17-(m-iodobenzoyloxy)-3-oxo-androsta-4,9(11)-diene-17β-carboxylic acid was crystallized from acetone; melting point 248°–249° C.; $[\alpha]_D=-31°$ (dioxan, c=0.1%); $\epsilon_{220}=36{,}000$.

890 mg of 17-(m-iodobenzoyloxy)-3-oxo-androsta-4,9(11)-diene-17β-carboxylic acid were gasified in 20 ml of ethyleneglycol with argon, treated with 4 g of potassium hydroxide and heated to 110° C. for 2.5 hours. After the addition of 6 ml of acetic acid, the mixture was poured into dilute hydrochloric acid and extracted with methylene chloride. The methylene chloride solutions were washed with water and dilute sodium chloride solution, dried and evaporated in vacuo. Chromatography on silica gel gave 17-hydroxy-3-oxo-androst-4,9(11)-diene-17β-carboxylic acid of melting point 267°–268° C.; $\epsilon_{240}$=17,240; $[\alpha]_D$=+58° (dioxan, c=0.1%). 17-hydroxy-3-oxo-androsta-4,9(11)-diene-17β-carboxylic acid is also obtained directly in the same manner from 9α-chloro-17(m-iodobenzoyloxy)-3-oxo-androst-4-ene-17β-carboxylic acid.

EXAMPLE II

From 17-(m-iodobenzoyloxy)-3-oxo-androst-4-ene-17β-carboxylic acid and methyl iodide there is obtained in dimethylacetamide, in the presence of sodium hydrogen carbonate, 17-(m-iodobenzoyloxy)-3-oxo-androst-4-ene-17β-carboxylic acid methyl ester of melting point 190°–191° C.; $[\alpha]_D$=−21° (dioxan, c=0.1%); $\epsilon_{222}$=36,300.

In a manner analogous to that described in Example I, from 17-(m-iodobenzoyloxy)-3-oxo-androst-4-ene-17β-carboxylic acid methyl ester, there is obtained 9α-chloro-17-(m-iodobenzoyloxy)-3-oxo-androst-4-ene-17β-carboxylic acid methyl ester [melting point 164°–166° C.; $[\alpha]_D$=−31° (dioxan, c=0.1%); $\epsilon_{221}$=33,200] and 17-(m-iodobenzoyloxy)-3-oxo-androsta-4,9(11)-diene-17β-carboxylic acid methyl ester of melting point 190°–191° C.; $[\alpha]_D$=−33° (dioxan, c=0.1%); $\epsilon_{222}$=36,900.

410 mg of 17-(m-iodobenzoyloxy)-3-oxo-androsta-4,9(11)-diene-17β-carboxylic acid methyl ester were gasified in 15 ml of 2-methoxyethanol with argon, treated with 3 g of potassium hydroxide and stirred at 80° C. for 50 minutes. The mixture was neutralized with 4.5 ml of acetic acid, poured into dilute hydrochloric acid and extracted three times with methylene chloride. The methylene solutions were washed with dilute sodium chloride solution, dried and evaporated in vacuo. Chromatography of the residue on silica gel gave 17-hydroxy-3-oxo-androsta-4,9(11)-diene-17β-carboxylic acid.

The last-mentioned acid can also be obtained under the same conditions from 9α-chloro-17(m-iodobenzoyloxy)-3-oxo-androst-4-ene-17β-carboxylic acid methyl ester.

The following example illustrates a pharmaceutical preparation containing the steroids provided by the present invention:

Example A

Tablets of the following compositions are produced in a manner known per se:

| | |
|---|---|
| Active ingredient, e.g., 9α-chloro-17-(m-iodobenzoyloxy)-3-oxo-androst-4-ene-17β-carboxylic acid methyl ester | 1 mg |
| Lactose | 60 mg |
| Starch | 37 mg |
| Talc | 1.8 mg |
| Magnesium Stearate | 0.2 mg |
| | 100.0 mg |

What is claimed is:
1. A steroid of the general formula:

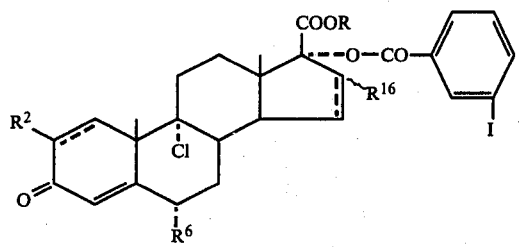

wherein R is hydrogen or lower alkyl, $R^2$ is hydrogen or chlorine, $R^6$ is hydrogen, fluorine or methyl, $R^{16}$ is hydrogen, α-methyl, ≠-methyl, methylene or α-hydroxy and the broken lines in the A and D-rings denote optional bonds with the proviso that the D-ring can be unsaturated only when $R^{16}$ is methyl.

2. The steroid of claim 1 which is 9α-chloro-17-(m-iodobenzoyloxy)-3-oxo-androst-4-ene-17β-carboxylic acid.

3. The steroid of claim 1 which is methyl 9α-chloro-17-(m-iodobenzoyloxy)-3-oxo-androst-4-ene-17β-carboxylate.

4. A steroid of the general formula:

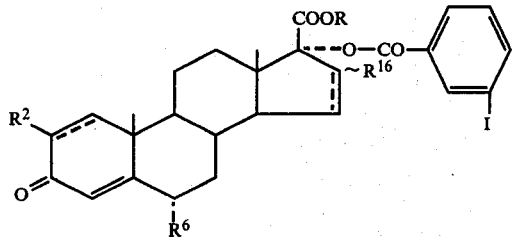

wherein R is hydrogen or lower alkyl, $R^2$ is hydrogen or chlorine, $R^6$ is hydrogen, fluorine or methyl, $R^{16}$ is hydrogen, α-methyl, β-methyl, methylene or α-hydroxy and the broken lines in the A and D rings denote optional bonds with the proviso that the D-ring can be unsaturated only when $R^{16}$ is methyl.

5. The steroid of claim 4 which is 17-(m-iodobenzoyloxy)-3-oxo-androst-4-ene-17β-carboxylic acid.

6. The steroid of claim 4 which is 17-(m-iodobenzoyloxy)-3-oxo-androst-4-ene-17β-carboxylic acid methyl ester.

* * * * *